(12) United States Patent
Boyle et al.

(10) Patent No.: US 6,939,362 B2
(45) Date of Patent: Sep. 6, 2005

(54) OFFSET PROXIMAL CAGE FOR EMBOLIC FILTERING DEVICES

(75) Inventors: William J. Boyle, Fallbrook, CA (US); John E. Papp, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 268 days.

(21) Appl. No.: 09/997,254

(22) Filed: Nov. 27, 2001

(65) Prior Publication Data

US 2003/0100917 A1 May 29, 2003

(51) Int. Cl.$^7$ .............................................. A61M 29/00
(52) U.S. Cl. ...................................................... 606/200
(58) Field of Search ................................ 606/200, 113, 606/114, 127, 159

(56) References Cited

U.S. PATENT DOCUMENTS

| | | | |
|---|---|---|---|
| 6,171,327 B1 | 1/2001 | Daniel et al. | |
| 6,214,026 B1 | 4/2001 | Lepak et al. | |
| 6,245,087 B1 | 6/2001 | Addis | |
| 6,277,138 B1 | 8/2001 | Levinson et al. | |
| 6,336,934 B1 | 1/2002 | Gilson et al. | |
| 6,402,771 B1 * | 6/2002 | Palmer et al. | 606/200 |
| 6,537,294 B1 * | 3/2003 | Boyle et al. | 606/200 |
| 2001/0012951 A1 | 8/2001 | Bates et al. | |
| 2002/0022858 A1 | 2/2002 | Demond et al. | |

FOREIGN PATENT DOCUMENTS

EP  1 103 233 A1  5/2001

OTHER PUBLICATIONS

U.S. Publication No.: 2001/0012951 A1, Mark C. Bates, et al., Emboli Filtration System Having Integral Strut Arrangement and Methods of Use, Publication Date Aug. 9, 2001.
U.S. Publication No.: 2002/0022858 A1, Jackson F. Demond, et al., Vascular Device for Emboli Removal Having Suspension Strut and Methods of Use, Publication Date Feb. 21, 2002.

* cited by examiner

Primary Examiner—Kevin T. Truong
(74) Attorney, Agent, or Firm—Fulwider Patton Lee & Utecht LLP

(57) ABSTRACT

An expandable cage used in conjunction with an embolic filtering device has a strut configuration including a proximal strut assembly coupled to a distal strut assembly. A filter can be attached to the distal strut assembly which has an inlet opening. The proximal strut assembly is "offset" from the distal strut assembly in that these proximal struts extend substantially along the vessel wall of the patient, rather than being "centered" in the body vessel when the cage is expanded in a body vessel. As a result, there is little cage structure directly in front of the opening of the filter, resulting in a virtually unobstructed opening for the filter.

23 Claims, 5 Drawing Sheets

OFFSET PROXIMAL CAGE FOR EMBOLIC FILTERING DEVICES

BACKGROUND OF THE INVENTION

The present invention relates generally to filtering devices used when an interventional procedure is being performed in a stenosed or occluded region of a body vessel to capture embolic material that may be created and released into the vessel during the procedure. The present invention is more particularly directed to an embolic filtering device made with an expandable cage or basket having good flexibility and bendability.

Numerous procedures have been developed for treating occluded blood vessels to allow blood to flow without obstruction. Such procedures usually involve the percutaneous introduction of an interventional device into the lumen of the artery, usually by a catheter. One widely known and medically accepted procedure is balloon angioplasty in which an inflatable balloon is introduced within the stenosed region of the blood vessel to dilate the occluded vessel. The balloon dilatation catheter is initially inserted into the patient's arterial system and is advanced and manipulated into the area of stenosis in the artery. The balloon is inflated to compress the plaque and press the vessel wall radially outward to increase the diameter of the blood vessel, resulting in increased blood flow. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

Another procedure is laser angioplasty which utilizes a laser to ablate the stenosis by super heating and vaporizing the deposited plaque. Atherectomy is yet another method of treating a stenosed body vessel in which cutting blades are rotated to shave the deposited plaque from the arterial wall. A catheter is usually used to capture the shaved plaque or thrombus from the bloodstream during this procedure.

In the procedures of the kind referenced above, abrupt reclosure may occur or restenosis of the artery may develop over time, which may require another angioplasty procedure, a surgical bypass operation, or some other method of repairing or strengthening the area. To reduce the likelihood of the occurrence of abrupt reclosure and to strengthen the area, a physician can implant an intravascular prosthesis for maintaining vascular patency, commonly known as a stent, inside the artery across the lesion. The stent can be crimped tightly onto the balloon portion of the catheter and transported in its delivery diameter through the patient's vasculature. At the deployment site, the stent is expanded to a larger diameter, often by inflating the balloon portion of the catheter.

The above non-surgical interventional procedures, when successful, avoid the necessity of major surgical operations. However, there is one common problem which can become associated with all of these non-surgical procedures, namely, the potential release of embolic debris into the bloodstream that can occlude distal vasculature and cause significant health problems to the patient. For example, during deployment of a stent, it is possible that the metal struts of the stent can cut into the stenosis and shear off pieces of plaque that can travel downstream and lodge somewhere in the patient's vascular system. Pieces of plaque material are sometimes generated during a balloon angioplasty procedure and become released into the bloodstream. Additionally, while complete vaporization of plaque is the intended goal during laser angioplasty, sometimes particles are not fully vaporized and enter the bloodstream. Likewise, not all of the emboli created during an atherectomy procedure may be drawn into the catheter and, as a result, enter the bloodstream as well.

When any of the above-described procedures are performed in the carotid arteries, the release of emboli into the circulatory system can be extremely dangerous and sometimes fatal to the patient. Debris carried by the bloodstream to distal vessels of the brain can cause cerebral vessels to occlude, resulting in a stroke, and in some cases, death. Therefore, although cerebral percutaneous transluminal angioplasty has been performed in the past, the number of procedures performed has been somewhat limited due to the justifiable fear of an embolic stroke occurring should embolic debris enter the bloodstream and block vital downstream blood passages.

Medical devices have been developed to attempt to deal with the problem created when debris or fragments enter the circulatory system following vessel treatment utilizing any one of the above-identified procedures. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists, making such a procedure in the carotid arteries a high-risk proposition.

Other techniques include the use of catheters with a vacuum source which provides temporary suction to remove embolic debris from the bloodstream. However, there can be complications associated with such systems if the vacuum catheter does not remove all of the embolic material from the bloodstream. Also, a powerful suction could cause trauma to the patient's vasculature.

Another technique which has had some success utilizes a filter or trap downstream from the treatment site to capture embolic debris before it reaches the smaller blood vessels downstream. The placement of a filter in the patient's vasculature during treatment of the vascular lesion can reduce the presence of the embolic debris in the bloodstream. Such embolic filters are usually delivered in a collapsed position through the patient's vasculature and then expanded to trap the embolic debris. Some of these embolic filters are self expanding and utilize a restraining sheath which maintains the expandable filter in a collapsed position until it is ready to be expanded within the patient's vasculature. The physician can retract the proximal end of the restraining sheath to expose the expandable filter, causing the filter to expand at the desired location. Once the procedure is completed, the filter can be collapsed, and the filter (with the trapped embolic debris) can then be removed from the vessel. While a filter can be effective in capturing embolic material, the filter still needs to be collapsed and removed from the vessel. During this step, there is a possibility that trapped embolic debris can backflow through the inlet opening of the filter and enter the bloodstream as the filtering system is being collapsed and removed from the patient. Therefore, it is important that any captured embolic debris remain trapped within this filter so that particles are not released back into the body vessel.

Some prior art expandable filters are attached to the distal end of a guide wire or guide wire-like member which allows the filtering device to be steered in the patient's vasculature as the guide wire is positioned by the physician. Once the guide wire is in proper position in the vasculature, the embolic filter can be deployed to capture embolic debris. The guide wire can then be used by the physician to deliver interventional devices, such as a balloon angioplasty dilatation catheter or a stent delivery catheter, to perform the interventional procedure in the area of treatment. After the procedure is completed, a recovery sheath can be delivered over the guide wire using over-the-wire techniques to collapse the expanded filter for removal from the patient's vasculature.

When a combination of an expandable filter and guide wire is utilized, it is important that the expandable filter portion remains flexible in order to negotiate the often tortuous anatomy through which it is being delivered. An expandable filter which is too stiff could prevent the device from reaching the desired deployment position within the patient's vasculature. As a result, there is a need to increase the flexibility of the expandable filter without compromising its structural integrity once in position within the patient's body vessel. Also, while it is beneficial if the area of treatment is located in a substantially straight portion of the patient's vasculature, sometimes the area of treatment is at a curved portion of the body vessel which can be problematic to the physician when implanting the expandable filter. If the expandable filter portion is too stiff, it is possible that the filter may not fully deploy within the curved portion of the body vessel. As a result, gaps between the filter and vessel wall can be formed which may permit some embolic debris to pass therethrough. Therefore, the filtering device should be sufficiently flexible to be deployed in, and to conform to, a tortuous section of the patient's vasculature, when needed.

Another problem presented to a physician utilizing an embolic filtering device is the possible undesired collection of embolic debris on the struts or ribs that form the cage onto which the filter is attached. The exposed surface of proximally located struts provide a potential area where embolic debris can stick, never reaching the filter positioned downstream from these struts. As the embolic filtering device is being collapsed for removal from the patient, it is possible for embolic debris which has become stuck to these struts to become dislodged and enter the blood stream. As a result, the design of the embolic filtering device itself may pose a danger if too many struts are located proximal to the filter since increased surface area will be exposed to the embolic particles. Therefore, it may be beneficial to use thin struts in the proximal region of the filtering device or to reduce the number of struts forming the self-expanding cage.

What has been needed is an expandable filter assembly having high flexibility with sufficient strength to be successfully deployed within a patient's vasculature to collect embolic debris which may be released into the patient's vasculature. Moreover, it would be beneficial if the design of the filtering device reduces the chances of embolic debris becoming stuck to the struts of the device, rather than being trapped within the filter. The present invention disclosed herein satisfies these and other needs.

SUMMARY OF THE INVENTION

The present invention provides a flexible cage or basket for use with an embolic filtering device designed to capture embolic debris created during the performance of a therapeutic interventional procedure, such as a balloon angioplasty or stenting procedure, in a body vessel. The present invention provides the physician with an embolic filtering device having good flexibility to allow it to be steered through tortuous anatomy, but yet possesses sufficient strength to hold open a filtering element against the wall of the body vessel for capturing embolic debris. The present invention creates an embolic filtering device that can be fully deployed within a body vessel and can provide a virtually unobstructed opening for the filtering element which captures embolic particles entrained in the body fluid. An embolic filtering device made in accordance with the present invention is relatively easy to deploy, has good visibility under flouroscopy, and has good flexibility and conformability to the patient's anatomy.

An embolic filter assembly of the present invention utilizes an expandable cage made from a self-expanding material, for example, nickel titanium (NiTi) or spring steel, and includes a number of outwardly extending struts capable of expanding from an unexpanded position having a first delivery diameter to an expanded or deployed position having a second implanted diameter. A filter element made from an embolic-capturing material is attached to the expandable cage to move between the unexpanded position and deployed position.

The struts of the cage can be set to remain in the expanded, deployed position until an external force is placed over the struts to collapse and move the struts to the unexpanded position. One way of accomplishing this is through the use of a restraining sheath, for example, which can be placed over the filtering device in a coaxial fashion to contact the cage and move the cage into the unexpanded position. The embolic filtering device can be implanted in the patient's vasculature and remain implanted for a period of time or can be attached to the distal end of an elongated member, such as a guide wire, for temporary placement in the vasculature. A guide wire may be used in conjunction with the filtering device when embolic debris is to be filtered during an interventional procedure. In this manner, the guide wire and filtering assembly, with the restraining sheath placed over the filter assembly, can be placed into the patient's vasculature. Once the physician properly manipulates the guide wire into the target area, the restraining sheath can be retracted to deploy the cage into the expanded position. This can be easily performed by the physician by simply retracting the proximal end of the restraining sheath (located outside of the patient). Once the restraining sheath is retracted, the self-expanding properties of the cage cause each strut to move in a outward, radial fashion away from the guide wire to contact the wall of the body vessel. As the struts expand radially, so does the filter element which will now be maintained in place to collect embolic debris that may be released into the bloodstream as the physician performs the interventional procedure. The guide wire is used by the physician to deliver the necessary interventional device into the area of treatment. The deployed filter element captures embolic debris created and released into the body vessel during the procedure.

In one aspect of the present invention, the enhanced flexibility and bendability of the embolic filtering device is achieved by utilizing a unique cage design which includes an offset proximal strut assembly attached to a distal strut assembly. A filtering element is attached to the distal strut assembly and is expandable within the body vessel for filtering purposes. The proximal strut assembly is said to be "offset" from the distal strut assembly in that these proximal struts extend substantially along the vessel wall of the patient, rather than being "centered" in the body vessel when expanded. As a result, there is little cage structure directly in front of the filter in the opened vessel, resulting in a virtually unobstructed opening for the filter.

In another aspect of the present invention, the offset proximal strut assembly is made from a pair of self-expanding struts which expand to contact the wall of the body vessel once implanted therein. The distal strut assembly also can be made from self-expanding struts. In this aspect of the invention, the unique cage design provides a wide entry opening for the emboli to be captured within the filtering element. This particular cage design also enhances wall apposition of the filter once deployed in the body vessel. The use of two offset struts to form the proximal strut assembly reduces the chances that emboli could stick to a strut or become lodged between struts forming the cage. Thus, the exposed surface area of the cage located proximal to the filter is greatly minimized which again helps to ensure that the embolic debris is directed through and captured by the filter.

In another aspect of the present invention, the cage has a modified distal strut assembly which creates a "wind sock" type of filter design that possesses good flexibility and bendability, yet possesses sufficient radial strength to maintain the filtering element in an open position once deployed in the body vessel.

It is to be understood that the present invention is not limited by the embodiments described herein. The present invention can be used in arteries, veins, and other body vessels. Other features and advantages of the present invention will become more apparent from the following detailed description of the invention, when taken in conjunction with the accompanying exemplary drawings.

DETAILED DESCRIPTION OF THE PREFERRED EMBODIMENTS

Figures 1, 2:
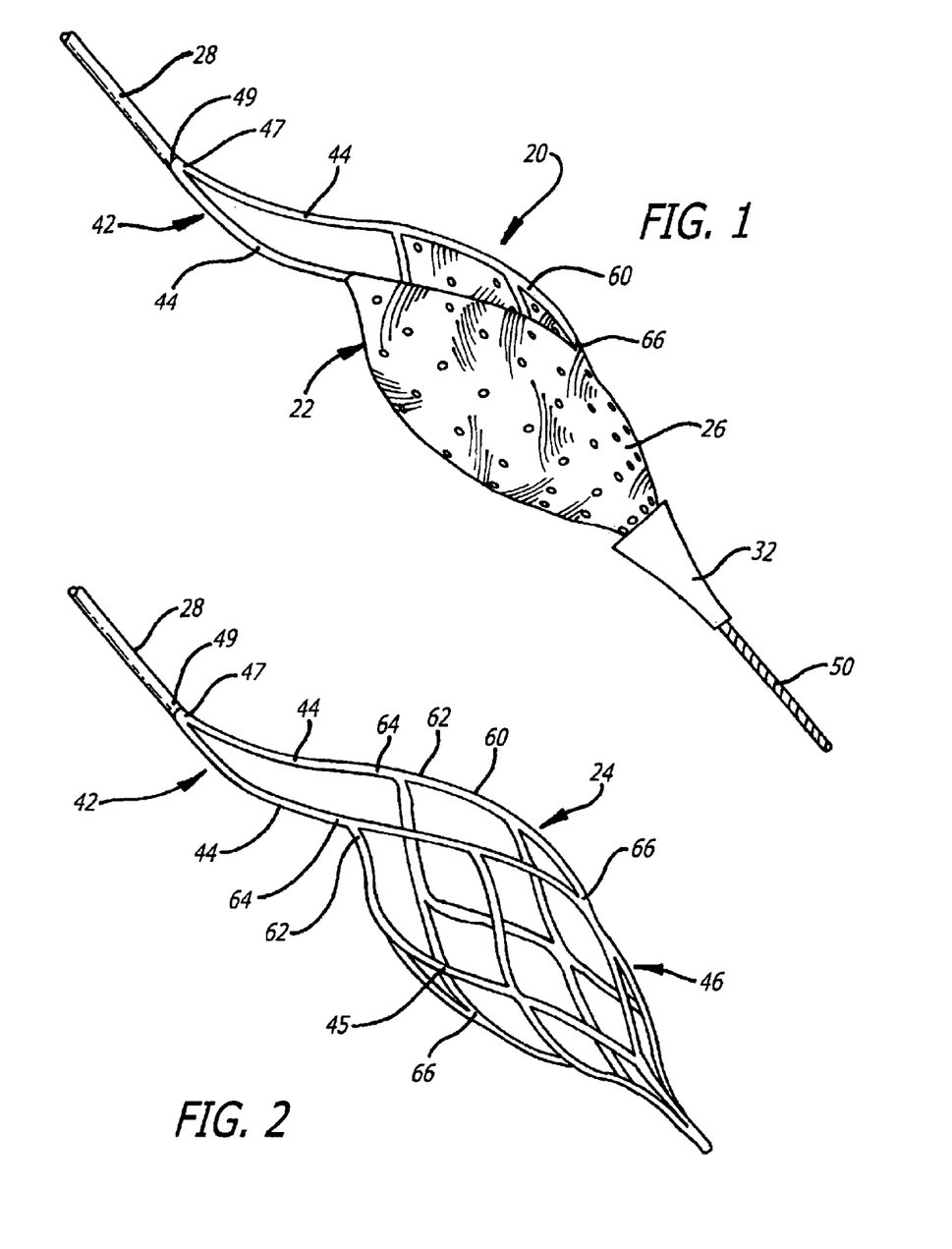
FIG. 1 is a perspective view of an embolic filtering device embodying features of the present invention.
FIG. 2 is a perspective view of the expandable cage which forms part of the embolic filtering device of FIG. 1.

Turning now to the drawings, in which like reference numerals represent like or corresponding elements in the drawings, FIGS. 1 and 2 illustrate one particular embodiment of an embolic filtering device 20 incorporating features of the present invention. This embolic filtering device 20 is designed to capture embolic debris which may be created and released into a body vessel during an interventional procedure. The embolic filtering device 20 includes an expandable filter assembly 22 having a self-expanding basket or cage 24 and a filter element 26 attached thereto. In this particular embodiment, the expandable filter assembly 22 is mounted on the distal end of an elongated tubular shaft, such as a guide wire 28. A restraining or delivery sheath 30 (FIG. 3) extends coaxially along the guide wire 28 to maintain the expandable filter assembly 22 in its unexpanded position until it is ready to be deployed within the patient's vasculature. The expandable filter assembly 22 is deployed by the physician by simply retracting the restraining sheath 30 proximally to expose the expandable filter assembly. Once the restraining sheath is retracted, the self-expanding cage 24 becomes uncovered and immediately begins to expand within the body vessel (see FIG. 4), causing the filter element 26 to expand as well.

An optional obturator 32 affixed to the distal end of the filter assembly 22 can be implemented to prevent possible "snowplowing" of the embolic filtering device as it is being delivered through the vasculature. The obturator can be made from a soft polymeric material, such as Pebax 40D, and preferably has a smooth surface to help the embolic filtering device travel through the vasculature and cross lesions while preventing the distal end of the restraining sheath 30 from "digging" or "snowplowing" into the wall of the body vessel.

Figure 3:
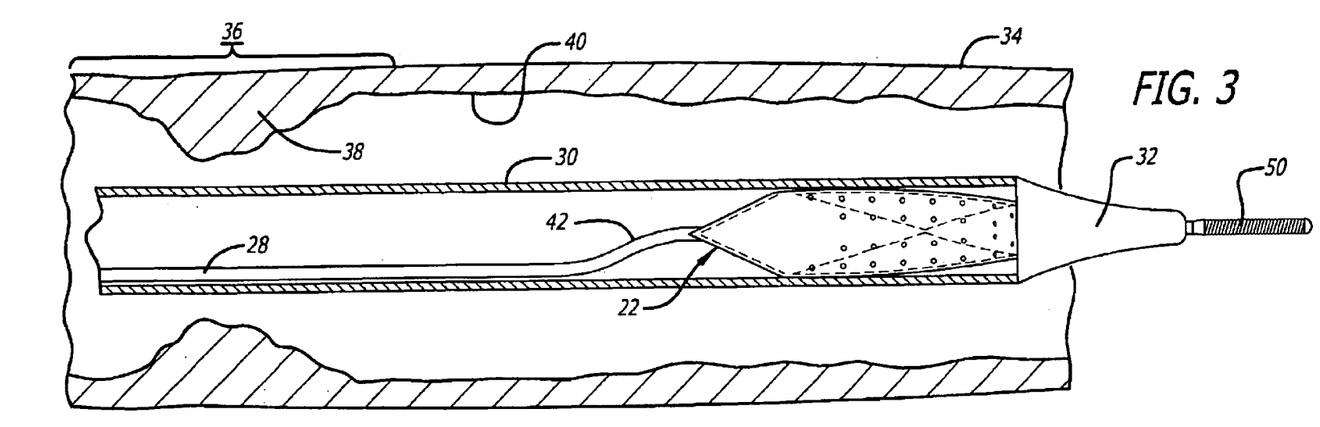
FIG. 3 is an elevational view, partially in cross section, of an embolic filtering device embodying features of the present invention as it is initially being delivered within a body vessel.
Figure 4:
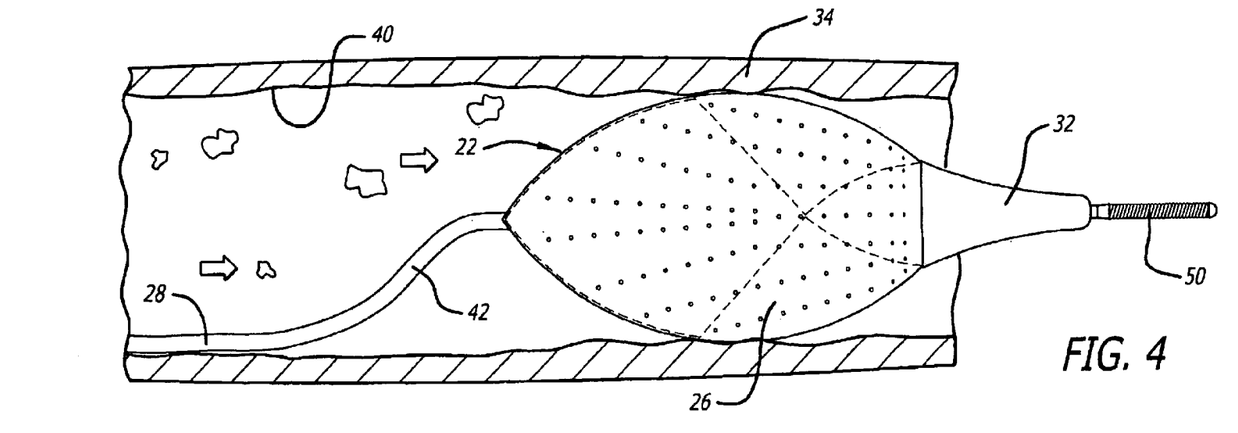
FIG. 4 is an elevational view, partially in cross section, similar to that shown in FIG. 3, wherein the embolic filtering device is deployed in its expanded, implanted position within the body vessel.

In FIGS. 3 and 4, the embolic filtering device 20 is shown as it is being delivered within an artery 34 or other body vessel of the patient. In FIG. 3, the embolic filtering device 20 is partially shown as it is being delivered through the patient's anatomy. This portion of the artery 34 has an area of treatment 36 in which atherosclerotic plaque 38 has built up against the inside wall 40 of the artery 34. The filter assembly 22 is placed distal to, and downstream from, the area of treatment 36. For example, the therapeutic interventional procedure may comprise the implantation of a stent (not shown) to increase the diameter of an occluded artery and increase the flow of blood therethrough. It should be appreciated that the embodiments of the embolic filtering device described herein are illustrated and described by way of example only and not by way of limitation. Also, while the present invention is described in detail as applied to an artery of the patient, those skilled in the art will appreciate that it can also be used in a variety of arteries or other body vessels, such as the coronary arteries, carotid arteries, renal arteries, saphenous vein grafts and other peripheral arteries. Additionally, the present invention can be utilized when a physician performs any one of a number of interventional procedures, such as balloon angioplasty, laser angioplasty or atherectomy which generally require an embolic filtering device to capture embolic debris created during the procedure.

The expandable cage 24 of the present invention includes self-expanding struts which, upon release from the restraining sheath, expand the filter element 26 into its deployed position within the artery (FIG. 4). Embolic debris created during the interventional procedure and released into the bloodstream are captured within the deployed filter element 26. Although not shown, a balloon angioplasty catheter can be initially introduced within the patient's vasculature in a conventional SELDINGER technique through a guiding catheter (not shown). The guide wire 28 is disposed through the area of treatment and the dilatation catheter can be advanced over the guide wire 28 within the artery 34 until the balloon portion is directly in the area of treatment 36. The balloon of the dilatation catheter can be expanded, expanding the plaque 38 against the wall 40 of the artery 34 to expand the artery and reduce the blockage in the vessel at the position of the plaque 38. After the dilatation catheter is removed from the patient's vasculature, a stent (not shown) can be implanted in the area of treatment 36 using over-the-wire or rapid exchange techniques to help hold and maintain this portion of the artery 34 and help prevent restenosis from occurring in the area of treatment. The stent could be delivered to the area of treatment on a stent delivery catheter (not shown) which is advanced from the proximal end of the guide wire to the area of treatment. Any embolic debris created during the interventional procedure will be released into the bloodstream and will enter the filter 26. Once the procedure is completed, the interventional device may be removed from the guide wire. The filter assembly 22 can also be collapsed and removed from the artery 34, taking with it any embolic debris trapped within the filter element 26. A recovery sheath (not shown) can be delivered over the guide wire 28 to collapse the filter assembly 22 for removal from the patient's vasculature.

The expandable cage 24, shown in FIGS. 1–4, includes a proximal offset strut assembly 42 having a pair of self-expanding struts 44 that extend radially outward from the unexpanded position, as shown in FIG. 3, to an expanded, implanted position shown in FIG. 4. The proximal strut assembly 42 is coupled to a distal strut assembly 46 which also includes a number of self-expanding struts 45 that extend radially out once placed in the expanded position. The filter element 26 is attached to the distal strut assembly 46 for filtering particles of emboli which may be released in the artery.

Figure 5:
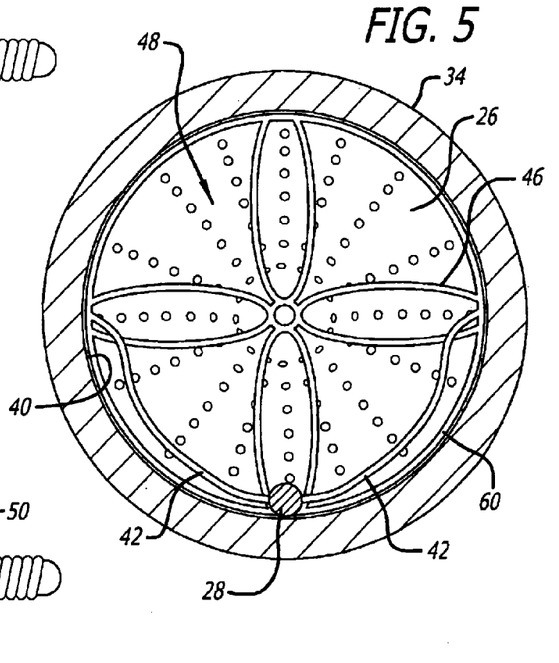
FIG. 5 is an end view of the embolic filtering device of FIG. 1 as it is deployed within a body vessel.

Referring specifically now to FIGS. 4 and 5, the proximal strut assembly 42 is shown as it is offset from the center line of the body vessel and with the distal strut assembly which is substantially centered within the body vessel. Referring to FIG. 5, it can be seen that the proximal offset strut assembly 42 extends from the guide wire 28 outwardly towards the distal strut assembly 46 substantially along the wall 40 of the body vessel. In this manner, there is little strut surface area located in the front of the inlet opening 48 of the distal strut assembly/filter where embolic particles can become lodged. The unique design of the expandable cage 24 thus allows the distal strut assembly 46 and filter element 26 to remain centered in the body vessel to provide proper wall apposition between filter and the body vessel, while the opening 48 remains virtually unobstructed by proximally located struts. The design of the expandable cage 24, as shown in FIGS. 1–4, provides an expandable means for deploying a filter element within the body vessel which is both flexible to reach tortuous paths in the patient's vasculature and maintains good wall apposition to prevent the possible discharge of embolic debris past the deployed filter element 26.

As is shown in FIG. 4, the filtering assembly 22 is to be placed at a downstream location from the area of treatment 36. This will allow the expandable cage 24 to assume its predetermined shape once the restraining sheath 30 is retracted from the filtering assembly 22. It should be appreciated that the guide wire 28, while shown extending along the vessel wall in FIG. 4, may itself become centered in the body vessel within the area of treatment once the medical device is used to perform the interventional procedure is placed in the area of treatment. However, if the filtering assembly 22 is positioned far enough from the area of treatment (greater than approximately 2 cm.), this centering of the guide wire within the area of treatment should not cause the distal most portion of the guide wire to lift from the vessel wall due to the flexibility and bendability of the guide wire. As a result, the chances that the expandable filter assembly 22 can be somewhat dislodged or misaligned to create a gap between the filter and body vessel after deployment is minimized.

As is shown in FIGS. 1 and 2, the expandable basket 24 is formed as an integral component with the guide wire 28. As such, the ends 47 of the struts 44 of the offset proximal strut assembly 42 are connected to the distal most end 49 of the guide wire 28. The distal end of the filter assembly 22 further includes a guide wire coil 50 which extends from the obturator 32. This guide wire coil 50 is bendable and allows the physician to maneuver the composite filtering device 20 into the desired area of the patient's vasculature. Both the obturator 32 and the guide wire coil 50 could be made from biocompatible, radiopaque materials to allow for better visualization under fluoroscopy. This particular design construction of the guide wire and guide wire coil results in a cage design which eliminates the presence of a segment of guide wire which would otherwise extend through the expandable basket 24. The design of the composite filtering assembly/basket thus is capable of being collapsed to a small delivery profile. The unique design of the expandable cage 24 still provides the benefits of a steerable guide wire while reducing the collapsed profile of the composite filtering assembly in order to reach tight distal vessels in the patient's anatomy.

Figure 6A:
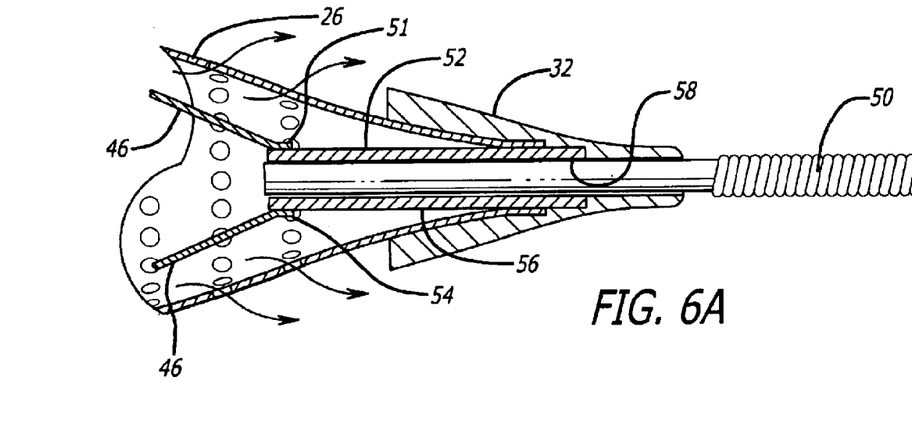
FIG. 6A is a side elevational view, partially in cross-section, showing the distal end of the embolic filtering device of FIG. 1.

Referring specifically now to FIG. 6A, the distal most end of the filtering assembly 22 is shown including the segment of guide wire coil 50 affixed to both the obturator 32 and distal strut assembly 46. A tubular member 52 extends through the obturator 32 to provide a stationary member used for mounting purposes. The end of the distal strut assembly 46 can terminate at a collar 54 which can be securely attached to the outer surface 51 of the tubular member 52. The filter element 26 is likewise affixed to the tubular member 52 to insure that no unwanted openings may develop at the end of the filtering assembly 22. A portion of the tubular member 52 is likewise bonded to the obturator 32 to create a composite unit which should not separate during usage. For example, the coil 50 can be bonded or adhesively secured to the inner surface 58 of the tubular member 52 as is shown in FIG. 6A. In this regard, the various components can be bonded utilizing suitable biocompatible adhesives known in the art or by utilizing other known fastening techniques known in the art.

Referring again back to FIGS. 1 and 2, the specific structure of the expandable cage 24 can be seen which helps to provide the unobstructed opening for the filter element 26. As can be seen best in FIG. 2, the distal strut assembly 46 includes an opening 60 which formed by a number of struts that make up the distal strut assembly 46. In the particular embodiment shown in FIGS. 1 and 2, the opening 60 is designed to articulate to its expanded position within the body vessel and to conform to the wall so that proper wall apposition will be maintained between the filter element 26 and the wall of the body vessel. In the disclosed embodiment, this opening 60 forms a pair of apices 62 to which the ends 64 of the struts 44 are attached. It should be appreciated that the proximal strut assembly could be either formed as a separate element which is attached to the distal strut assembly 46, which would allow the proximal strut assembly to be made from a different material from the distal strut assembly. Alternatively, the two strut assemblies 42 and 44 could also be formed as a composite unit from a single piece of material.

The opening 60 includes a pair of hinge portions 66 which allow the opening 60 to open and close. These hinge portions 66 act like mechanical hinges in the opening and closing of the distal strut assembly 46. As is shown in FIG. 1, the filter element 26 can be formed in such a manner to allow it to be adhesively bonded or otherwise secured to the struts forming the distal strut assembly 46. In this manner, the opening 60 of the distal strut assembly 46 creates the inlet opening for the filter element 26. Again, as is shown in FIG. 5, the location of the proximal strut assembly 42 along the wall of the body vessel creates a virtually unobstructed opening for embolic particles to enter into the filter element 26. It should be appreciated that other designs could be utilized in conjunction with the proximal and distal strut assemblies without departing from the spirit and scope of the present invention.

Figure 7:
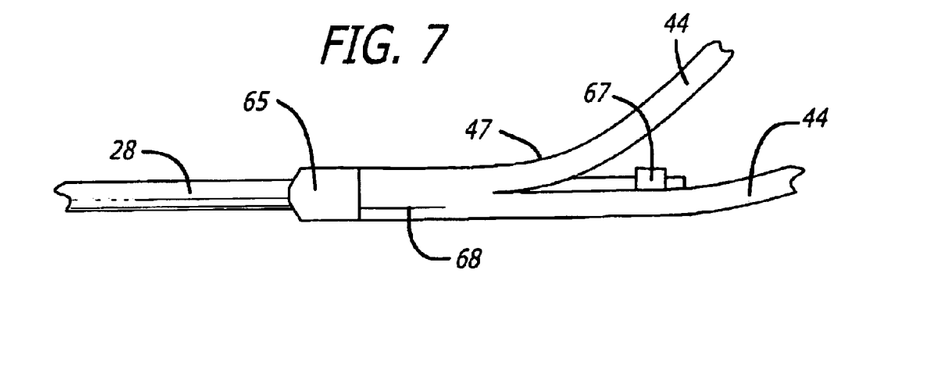
FIG. 7 is a side elevational view showing the proximal end of another embodiment of an expandable cage as it is mounted to an elongated member, such as guide wire.

Referring now to FIG. 7, an alternative mechanism for attaching the proximal end of the guide wire 28 to the proximal strut assembly 46 is shown. In this particular example, the ends 47 of the struts 44 are joined at a collar 68 which extends over a portion of the guide wire 28. The use of the collar 68 allows the guide wire 28 to spin freely allowing the filtering assembly 22 to remain stationary in the body vessel even if the proximal end of the guide wire is rotated accidentally by the physician during usage. As a result, the filtering assembly 22 should not rotate in the body vessel which will prevent possible trauma to the wall of the body vessel. The collar 68 is situated between a pair of stop fittings 65 and 67 located on the guide wire 28 which maintains the collar 68 in place. This is one way in which the embolic filtering assembly 22 can be rotatably mounted onto an elongated member, such as a guide wire.

Figure 7A:
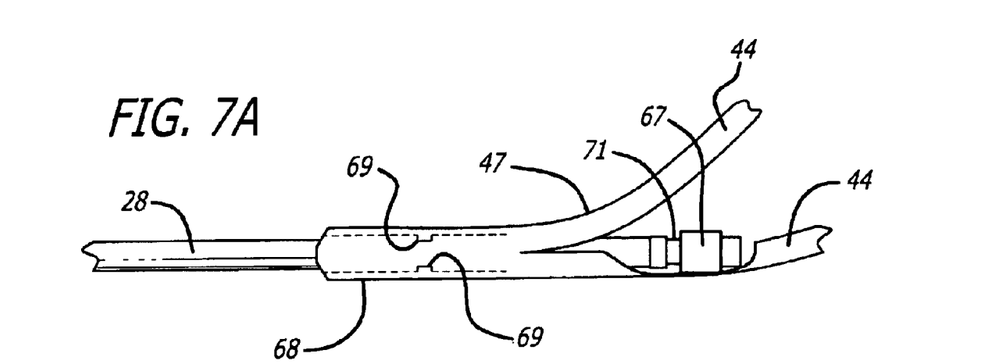
FIG. 7A is a side elevational view, partially fragmented, showing the proximal end of an expandable cage as it is slidably mounted to an elongated member, such as guide wire.
Figure 7B:
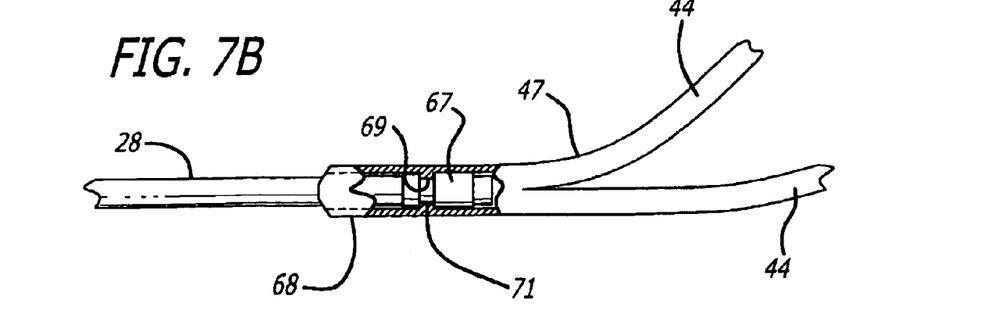
FIG. 7B is a side elevational view, partially in cross-section and fragmented, of the proximal end of the embodiment of FIG. 7A as it is affixed to the distal fitting mounted on the guide wire.

Referring now to FIGS. 7A and 7B, an alternative mechanism for attaching the proximal end of the strut assembly 46 to the guide wire 28 is shown. In this particular embodiment, the proximal collar 68 is not initially fixedly mounted to the guide wire 28. Rather, the offset cage design could be backloaded over the proximal end of the guide wire 28 through the inner diameter of the collar 68. The delivery system could be a rapid exchange device which could consist of a stiff support structure (not shown) which allows the physician to advance the collapsed filter assembly over the guide wire to the intended site within the body. In this manner, the collapsed filter assembly could be initially kept at the proximal end of the guide wire until the physician has maneuvered the distal end of the guide wire into the target in the patient. Then, the physician would simply slide the rapid exchange device with the collapsed filter assembly to the distal end of the guide wire where the cage could be snap-fitted onto the distal fitting 67. Tabs 69 located on the collar 68 could be positioned such that the cage 24 would attach to the distal fitting 67 located on the guide wire 28. As is seen in FIGS. 7A and 7B, the distal fitting 67 may include an annular recess 71 which receives one or more of the tabs 69 formed on the collar 68. In this regard, the physician simply snaps the tabs into the recess 71 by pushing the rapid exchange device and collapsed filter assembly distally along the guide wire 28 to contact the fitting 67. As shown in FIG. 7B, the fitting 67 is large enough to abut the collar 68 and prevent the collar from moving past the fitting during usage. It should be appreciated that the tab 69 could be formed in other shapes and sizes, such as an annular ring, which would extend from the inner surface of the collar 68 and would be adapted to fit within the annular recess of the distal fitting. It also should be appreciated that other snap mechanisms could be utilized in order to attach the proximal collar 68 to the fitting 67. The particular snap mechanism shown in FIGS. 7A and 7B still allows the expandable cage 24 to spin freely at the end of the fitting, allowing the cage to spin freely relative to the guide wire 28.

Figure 8:
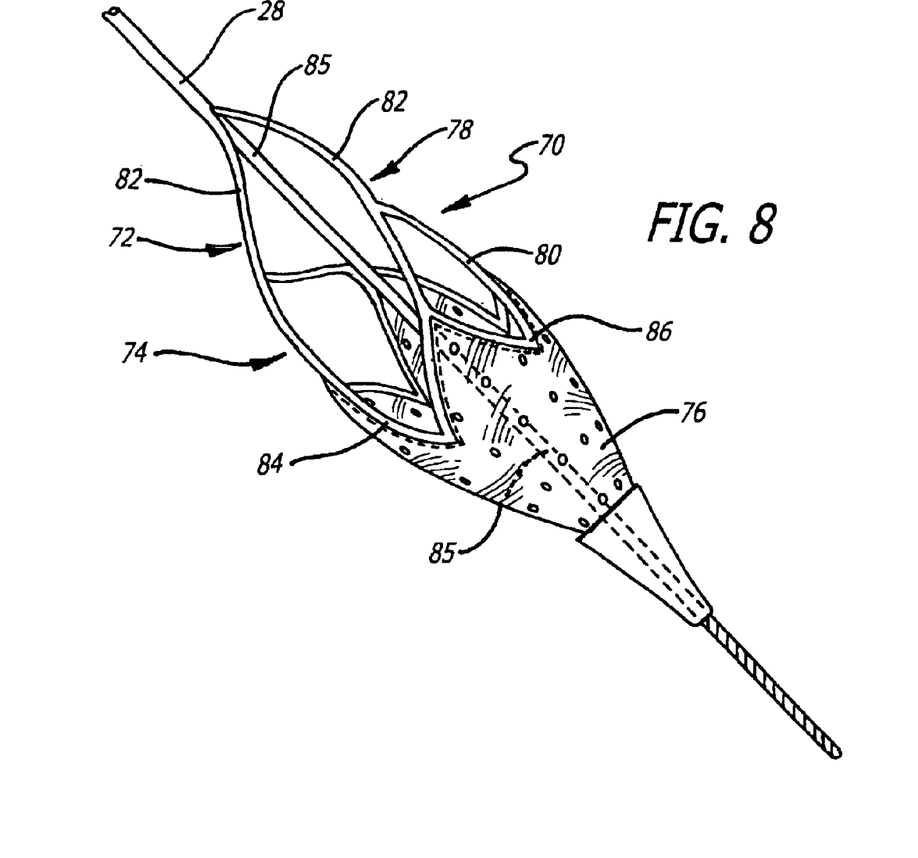
FIG. 8 is a perspective view of another embodiment of an embolic filtering device made in accordance with the present invention.
Figure 9:
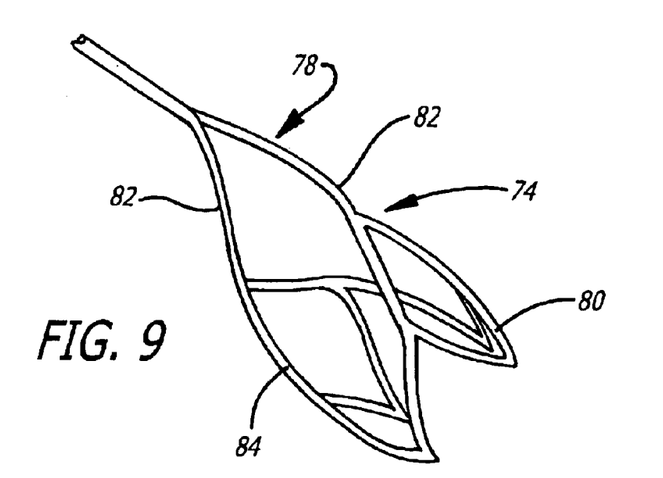
FIG. 9 is a perspective view of the expandable cage which forms part of the embolic filtering device of FIG. 8.

An alternative embodiment of an embolic protection device 70 made in accordance with the present invention is shown in FIGS. 8 and 9. In this particular embodiment, the embolic filtering device 70 includes an expandable filter assembly 72 having a modified version of a self-expanding cage 74 utilized to deploy the filter assembly 72 from the unexpanded position to the expanded position. This filter assembly 72 includes a filter element 76 attached to the self-expanding cage 74. This particular embodiment of the expandable cage 74 is similar to the embodiment shown in FIGS. 1–5 in that the cage 74 includes an offset proximal strut assembly 78 coupled to a distal strut assembly 80. The proximal strut assembly 78 is offset from the distal strut assembly 80 in a manner that the struts 82 making up the proximal strut assembly 78 are adapted to extend along the wall of the body vessel when the filter assembly 72 is deployed in the patient's vasculature. This distal strut assembly 80 is a modified version of the previously described distal strut assembly 46 shown in FIGS. 1–5. In this embodiment, the distal most struts of this distal strut assembly 80 have been removed to create a shortened expandable cage 74. The filter element 76 connected to the struts 84 of the distal strut assembly 80 creates a "windsock" type of filter design since there is a lack of a strut assembly extending to the obturator 32. As can be seen in FIG. 8, the filter element 76 takes on somewhat of a tulip-like shape as it is attached to the struts 84 forming the distal strut assembly 80. In this regard, the distal strut assembly 80 includes an opening 86 formed by struts which extend and conform to the wall of the body vessel once implanted therein. The proximal end of the filter element 76 is in turn attached to the opening 86 formed by the distal strut assembly 80 for the collection of embolic particles which may be entrained in the body fluid. The filter may have an opening similar to that shown in FIG. 1.

Additionally, a support wire 85 could be attached to the guide wire 28 and extend out to the tip coil 50. In this embodiment, the support wire 85 would be centered in and extend to the tip coil 50 once inside the cage 74. This embodiment could include the proximal connection shown in FIG. 1 along with the distal connection shown in FIG. 6B. This particular configuration allows the cage 74 to freely rotate on the guide wire and would still allow the wire to rotate the coil tip 50 independently from the cage and delivery sheath. The advantage of this particular arrangement allows the physician to shape the tip coil and steer the guide wire through difficult bends and branches of the vessels by pushing and rotating the guide wire. In this manner, the physician maintains the steerability of the guide wire from proximal end to distal coil tip.

Alternatively, this same support wire 85 could be attached to the filtering device shown in FIGS. 1 and 2. Again, the expandable cage would still be rotatably fixed to the guide wire but the guide wire would still be steerable to allow the physician to steer the coil tip to implant the filter assembly into the desired location in the patient's vasculature.

It should be appreciated that the support wire is shown as a separate length of material, which allows it to have a smaller outer diameter from the guide wire 28 to reduce the profile of the filter assembly when collapsed. However, the guide wire and support wire could be made from a continuous piece of wiring, if desired. Additionally, when a separate length of wiring is used to form the support wire, a more elastic material than the guide wire could be used to prevent the filter assembly from becoming too stiff.

Figure 6B:
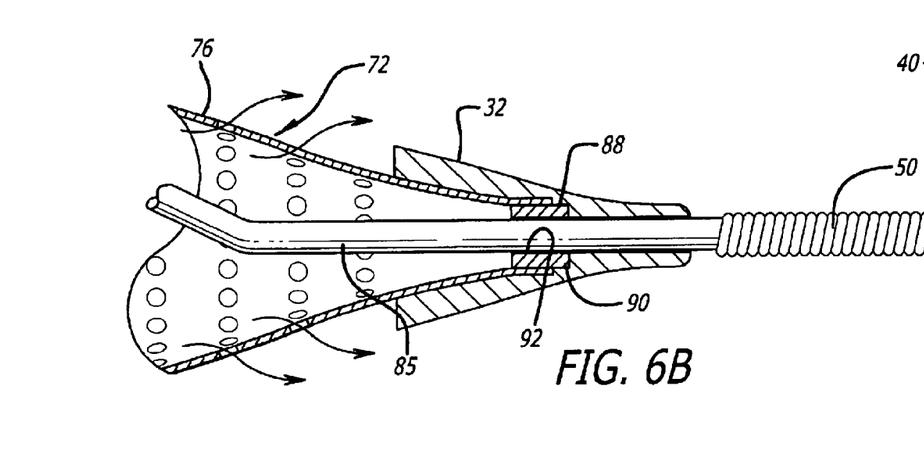
FIG. 6B is a side elevational view, partially in cross-section, showing the distal end of the embolic filtering device of FIG. 8.

Referring now to FIG. 6B, the connection of the distal end of the filter element 76 in shown in greater detail. The connection of the various elements at the distal end of the filtering assembly 72 is similar to the design shown in FIG. 6A. As can be seen in FIG. 6B, the filter element 76 tapers down to a distal end which is attached to the outer surface 88 of a mounting member 90 utilized for mounting the components together. The obturator 32 can be adhesively bonded to this outer surface 88 as well. A guide wire coil 50 can likewise extend past the obturator. Since the guide wire can be rotated by the physician, the wire 85 would not be bonded to the mounting member 90 in this particular embodiment, but should remain free to rotate and slide within the mounting member. In this embodiment, suitable bonding materials known in the art can be utilized to connect the various elements together. Alternatively, other fastening techniques known in the art could be utilized for connecting the components together.

The expandable cage of the present invention can be made in many ways. One particular method of making the cage is to cut a thin-walled tubular member, such as nickel-titanium hypotube, to remove portions of the tubing in the desired pattern for each strut, leaving relatively untouched the portions of the tubing which are to form each strut. The tubing may be cut into the desired pattern by means of a machine-controlled laser. Prior to laser cutting the strut pattern, the tubular member could be formed with varying wall thicknesses which will be used to create the flexing portions of the cage.

The tubing used to make the cage could possible be made of suitable biocompatible material such as spring steel. Elgiloy is another material which could possibly be used to manufacture the cage. Also, very elastic polymers could be used to manufacture the cage.

The strut size is often very small, so the tubing from which the cage is made must necessarily have a small diameter. Typically, the tubing has an outer diameter on the order of about 0.020–0.040 inches in the unexpanded condition.

The wall thickness of the tubing is usually about 0.076 mm (0.001–0.006 inches). As can be appreciated, the strut depth at the bending points will be less. For cages implanted in body lumens, such as PTA applications, the dimensions of the tubing maybe correspondingly larger. While it is preferred that the cage be made from laser cut tubing, those skilled in the art will realize that the cage can be laser cut from a flat sheet and then rolled up in a cylindrical configuration with the longitudinal edges welded to form a cylindrical member.

Generally, the tubing is put in a rotatable collet fixture of a machine-controlled apparatus for positioning the tubing relative to a laser. According to machine-encoded instructions, the tubing is then rotated and moved longitudinally relative to the laser which is also machine-controlled. The laser selectively removes the material from the tubing by ablation and a pattern is cut into the tube. The tube is therefore cut into the discrete pattern of the finished struts. The cage can be laser cut much like a stent is laser cut. Details on how the tubing can be cut by a laser are found in U.S. Pat. No. 5,759,192 (Saunders), U.S. Pat. No. 5,780,807 (Saunders) and U.S. Pat. No. 6,131,266 (Saunders) which have been assigned to Advanced Cardiovascular Systems, Inc.

The process of cutting a pattern for the strut assembly into the tubing generally is automated except for loading and unloading the length of tubing. For example, a pattern can be cut in tubing using a CNC-opposing collet fixture for axial rotation of the length of tubing, in conjunction with CNC X/Y table to move the length of tubing axially relative to a machine-controlled laser as described. The entire space between collets can be patterned using the $CO_2$ or Nd:YAG laser set-up. The program for control of the apparatus is dependent on the particular configuration used and the pattern to be ablated in the coding.

A suitable composition of nickel-titanium which can be used to manufacture the strut assembly of the present invention is approximately 55% nickel and 45% titanium (by weight) with trace amounts of other elements making up about 0.5% of the composition. The austenite transformation temperature is between about 0° C. and 20° C. in order to achieve superelasticity. The austenite temperature is measured by the bend and free recovery tangent method. The upper plateau strength is about a minimum of 60,000 psi with an ultimate tensile strength of a minimum of about 155,000 psi. The permanent set (after applying 8% strain and unloading), is approximately 0.5%. The breaking elongation is a minimum of 10%. It should be appreciated that other compositions of nickel-titanium can be utilized, as can other self-expanding alloys, to obtain the same features of a self-expanding cage made in accordance with the present invention.

In one example, the cage of the present invention can be laser cut from a tube of nickel-titanium (Nitinol) whose transformation temperature is below body temperature. After the strut pattern is cut into the hypotube, the tubing is expanded and heat treated to be stable at the desired final diameter. The heat treatment also controls the transformation temperature of the cage such that it is super elastic at body temperature. The transformation temperature is at or below body temperature so that the cage is superelastic at body temperature. The cage is usually implanted into the target vessel which is smaller than the diameter of the cage in the expanded position so that the struts of the cage apply a force to the vessel wall to maintain the cage in its expanded position. It should be appreciated that the cage can be made from either superelastic, stress-induced martensite NiTi or shape-memory NiTi.

Another way of making the cage of the present device is to utilize a shape-memory material, such as nickel titanium, which has the struts cut utilizing a machine-controlled laser. A tubular piece of material could be utilized in this process. The cage could be manufactured to remain in its open position while at body temperature and would move to its unexpanded position upon application of a low temperature. One suitable method to allow the cage to assume a change phase which would facilitate the strut and filter assembly being mounted into the restraining sheath include chilling the filter assembly in a cooling chamber maintained at a temperature below the martensite finish temperature through the use of liquid nitrogen. Once the cage is placed in its collapsed state, the restraining sheath can be placed over the cage to prevent the cage from expanding once the temperature is brought up to body temperature. Thereafter, once the filtering device is to be utilized, the restraining sheath is simply retracted to allow the cage to move to its expanded position within the patient's vasculature. If super elastic NiTi is used, the cage/filter assembly can be simply back loaded into the restraining sheath. The cage would be "set" to the expanded position.

The cage could also be manufactured by laser cutting a large diameter tubing of nickel-titanium which would create the cage in its expanded position. Thereafter, the formed cage could be placed in its unexpanded position by backloading the cage into a restraining sheath which will keep the device in the unexpanded position until it is ready for use. If the cage is formed in this manner, there would be no need to heat treat the tubing to achieve the final desired diameter. This process of forming the cage could be implemented when using superelastic nickel-titanium or shape-memory nickel-titanium.

The struts forming the struts of the proximal strut assembly can be made from the same or a different material than the distal strut assembly. In this manner, the additional or less flexibility for the proximal strut assembly can be obtained. When a different material is utilized for the struts of the distal proximal strut, the distal strut assembly can be manufactured through the lazing process described above with the struts of the proximal strut assembly being formed separately and attached to the distal assembly. Suitable fastening means such as adhesive bonding, brazing, soldering, welding and the like can be utilized in order to connect the struts to the distal assembly. Suitable materials for the struts include superelastic materials, such as nickel-titanium, spring steel, Elgiloy, along with polymeric materials which are sufficiently flexible and bendable. Also, although two struts are shown forming the proximal strut assembly in the disclosed embodiments, it will be appreciated by those skilled in the art that additional struts could also be utilized to form this assembly without departing from the spirit and scope of the present invention.

The polymeric material which can be utilized to create the filtering element include, but is not limited to, polyurethane and Gortex, a commercially available material. Other possible suitable materials include ePTFE. The material can be elastic or non-elastic. The wall thickness of the filtering element can be about 0.00050–0.0050 inches. The wall thickness may vary depending on the particular material selected. The material can be made into a cone or similarly sized shape utilizing blow-mold technology. The openings can be any different shape or size. A laser, a heated rod or other process can be utilized to create to perfusion openings in the filter material. The holes, would of course be properly sized to catch the particular size of embolic debris of interest. Holes can be lazed in a spinal pattern with some similar pattern which will aid in the re-wrapping of the media during closure of the vice. Additionally, the filter material can have a "set" put in it much like the "set" used in dilatation balloons to make the filter element re-wrap more easily when placed in the collapsed position.

The materials which can be utilized for the restraining sheath can be made from polymeric material such as cross-linked HDPE. This sheath can alternatively be made from a material such as polyolifin which has sufficient strength to hold the compressed strut assembly and has relatively low frictional characteristics to minimize any friction between the filtering assembly and the sheath. Friction can be further reduced by applying a coat of silicone lubricant, such as Microglide®, to the inside surface of the restraining sheath before the sheaths are placed over the filtering assembly.

Further modifications and improvements may additionally be made to the device and method disclosed herein without departing from the scope of the present invention. Accordingly, it is not intended that the invention be limited, except as by the appended claims.

What is claimed is:

1. A cage for an embolic filtering de ice used to filter embolic particles from a body vessel, comprising:
   a proximal strut assembly connected to a distal strut assembly which together extend along a longitudinal axis and are both movable between an unexpanded position and an expanded position, the distal strut assembly having an inlet opening which expands and forms an outer periphery of the cage when placed in the expanded position; wherein the proximal strut assembly is adapted to extend substantially along the outer periphery in a parallel relationship with the longitudinal axis when placed in the expanded position and the proximal strut assembly is adapted to be rotatably attached to an elongated member.

2. The cage of claim 1, wherein a filter member is attachable to the distal strut assembly.

3. The cage of claim 1, wherein the proximal strut assembly includes a plurality of expandable struts each having a first end and a second end, the second ends of the struts being attached to the distal strut assembly and the first ends being adapted for attachment to an elongated member.

4. The cage of claim 3, wherein the distal strut assembly includes a plurality of expandable struts, wherein struts of the distal strut assembly are arranged to form the inlet opening of the distal strut assembly.

5. The cage of claim 1, wherein the proximal strut assembly includes a pair of self-expanding struts.

6. The cage of claim 5, wherein each strut of the proximal strut assembly has a first end and a second end, the second ends of the strut being attached to the distal strut assembly and the first ends being adapted for attachment to an elongated member.

7. An embolic filtering device used to filter embolic particles from a body vessel, comprising:
   an elongated member;
   a filtering assembly rotatably attached to the elongated member and movable between an unexpanded position and an expanded position, the filtering assembly including an expandable cage and a filter member attached to the expandable cage, the expandable cage extending along a longitudinal axis and including a proximal strut assembly connected to a distal strut assembly, the fitter member being attached to the distal strut assembly, wherein the distal strut assembly has an inlet opening which expands and forms an outer periphery of the cage to allow embolic particles to enter the filter member and the proximal strut assembly is adapted to extend substantially along the outer periphery in a parallel relationship with the longitudinal axis when placed in the expanded position.

8. The embolic filtering device of claim 7, further including means for rotatably attaching the proximal strut assembly to the elongated member.

9. The embolic filtering device of claim 7, wherein the elongated member is a guide wire.

10. The embolic filtering device of claim 7, wherein the proximal strut assembly includes a plurality of expandable struts each having a first end and a second end, the second ends of the struts being attached to the distal strut assembly and the first ends being adapted for attachment to an elongated member.

11. The embolic filtering device of claim 10, wherein the distal strut assembly includes a plurality of expandable struts, wherein struts of the distal strut assembly are arranged to form the inlet opening of the distal strut assembly.

12. The embolic filtering device of claim 7, wherein the proximal strut assembly includes a pair of self-expanding struts.

13. The embolic filtering device of claim 12, wherein each strut of the proximal strut assembly has a first end and a second end, the second ends of the struts being attached to the distal strut assembly and the first ends being adapted for attachment to the elongated member.

14. The embolic filtering device of claim 13, further including a segment of coil wire attached to and extending from the distal strut assembly.

15. The embolic filtering device of claim 14, further including an obturator attached to and extending from the distal strut assembly.

16. A method for implanting an embolic filtering device in a body vessel of a patient for filtering embolic particles entrained in the patient's body fluid, comprising:

providing a filtering assembly rotatably attached to a guide wire and movable between an unexpanded position and an expanded position, the filtering assembly extending along a longitudinal axis and including an expandable cage and a filter member attached to the expandable cage, the expandable cage including a proximal strut assembly connected to a distal strut assembly, the filter member being attached to the distal strut assembly, wherein the distal strut assembly has an inlet opening which expands to form an outer periphery of the filtering assembly and conforms to the wall of the body vessel to allow embolic particles to enter the filter member an the proximal strut assembly is adapted to extend substantially along the wall of the body vessel and the periphery of the filtering assembly in a parallel relationship with the longitudinal axis when placed in the expanded position;

maintaining the filtering assembly in the unexpanded position;

maneuvering the filtering assembly into the desired location in the patient; and moving the filtering assembly into the expanded position.

17. The method of claim 16, wherein the guide wire is used to maneuver the filtering assembly in the patient.

18. The method of claim 17, wherein the retractable sheath is retracted to move the filtering assembly into the expanded position.

19. The method of claim 18, wherein the proximal strut assembly has two self-expanding struts which extend along the wall of the body lumen when placed in the expanded position.

20. The method of claim 16, wherein a retractable sheath is used to maintain the filtering assembly in the unexpanded position.

21. A cage for an embolic filtering device used to filter embolic particles from a body vessel, comprising:

a proximal strut assembly connected to a distal strut assembly which together extend along a longitudinal axis and are both movable between an unexpanded position and an expanded position, the distal strut assembly having an inlet opening which expands to form an outer periphery of the cage and conforms to the wall of the body vessel when placed in the expanded position; wherein the proximal strut assembly is adapted to extend substantially along the periphery in a parallel relationship with the longitudinal axis when placed in the expanded position and the proximal strut assembly is made from a different material than the distal strut assembly.

22. An embolic filtering device used the filter embolic particles from a body vessel, comprising:

an elongated member;

a filtering assembly attached to the elongated member an movable between an unexpanded position and an expanded position, the filtering assembly including an expandable cage and a filter member attached to the expandable cage, the expandable cage extending along a longitudinal axis and including a proximal strut assembly connected to a distal strut assembly, the proximal strut assembly being made from a different material than the distal strut assembly, the filter member being attached to the distal strut assembly, wherein the distal strut assembly has an inlet opening which expands to form an outer periphery of the cage and conforms to the wall of the body vessel to allow embolic particles to enter the filter member and the proximal strut assembly is adapted to extend substantially along the outer periphery in a parallel relationship with the longitudinal axis when placed in the expanded position.

23. An embolic filtering device used to filter embolic particles from a body vessel, comprising:

an elongated member;

a filtering assembly attached to the elongated member an movable between an unexpanded position and an expanded position, the filtering assembly including an expandable cage and a filter member attached to the expandable cage, the expandable cage extending alone a longitudinal axis and including a proximal strut assembly connected to a distal strut assembly, the filter member being attached to the distal strut assembly, wherein the distal strut assembly has an inlet opening which expands to form an outer periphery of the cage and conforms to the wall of the body vessel to allow embolic particles to enter the filter member and the proximal strut assembly is adapted to extend substantially along the outer periphery in a parallel relationship with the longitudinal axis when placed in the expanded position, the elongated member extending through the length of the expandable cage to the distal end of the assembly and including a distal tip coil that extends distally from the expandable cage.

* * * * *

UNITED STATES PATENT AND TRADEMARK OFFICE
CERTIFICATE OF CORRECTION

PATENT NO.    : 6,939,362 B2
DATED         : September 6, 2005
INVENTOR(S)   : William J. Boyle et al.

It is certified that error appears in the above-identified patent and that said Letters Patent is hereby corrected as shown below:

Column 4,
Line 11, delete "flouroscopy" and insert -- fluoroscopy --.

Column 8,
Line 6, delete "device is used" and insert -- device used --.

Column 11,
Line 41, delete "possible" and insert -- possibly --.

Column 13,
Line 49, delete "to create to" and insert -- to create --.

Column 14,
Line 7, delete "de ice" and insert -- device --.

Column 16,
Lines 17 and 39, delete "elongated member an" and insert -- elongated member and --.
Line 43, delete "alone" and insert -- along --.

Signed and Sealed this

Seventh Day of February, 2006

JON W. DUDAS
*Director of the United States Patent and Trademark Office*